United States Patent [19]

Redpath et al.

[11] Patent Number: 4,929,636
[45] Date of Patent: May 29, 1990

[54] POSITIVE INOTROPHIC BENZOTHIAZOLE AND BENZOTHIOPHENE COMPOSITIONS AND METHOD OF USE THEREFOR

[75] Inventors: James Redpath, Bishopbriggs; Robert T. Logan, Lanark; David B. McFadzen, Hamiltom; Robert G. Roy, Larkhall, all of Scotland

[73] Assignee: Akzo N.V., Arnhem, Netherlands

[21] Appl. No.: 333,806

[22] Filed: Apr. 6, 1989

Related U.S. Application Data

[60] Continuation of Ser. No. 140,953, Dec. 28, 1987, abandoned, which is a continuation of Ser. No. 466, Jan. 5, 1987, abandoned, which is a division of Ser. No. 709,396, Mar. 7, 1985, Pat. No. 4,665,206.

[30] Foreign Application Priority Data

Mar. 16, 1984 [GB] United Kingdom ............... 8406906

[51] Int. Cl.$^5$ ............... A61K 31/425; A61K 31/38; A61K 31/36
[52] U.S. Cl. ............................. 514/443; 514/366; 514/367
[58] Field of Search ............... 514/366, 367, 443

[56] References Cited

U.S. PATENT DOCUMENTS 2,775,593 12/1956 Behnisch et al. ................ 260/279
4,249,014 2/1981 Robba et al. ..................... 549/49

FOREIGN PATENT DOCUMENTS 1229580 12/1967 United Kingdom .
1231170 12/1967 United Kingdom .

OTHER PUBLICATIONS

Goodman and Gilman, "The Pharmacological Basin of Therapeutics", 7th Ed., p. 7/6 (1985).
Cheng, "The International Textbook of Cardiology", Pergamon Press, p. 1047 (1986).
Breckenridge, "Drugs in the Management of Heart Disease", MTP Press, p. 159 (1985).
Chemische Berichte, K. Wagner et al., "Synthesis and Reactivity of 2-Alkoxycarbonylbenzothiazole N-Oxides," vol. 106, No. 2 (1973), pp. 639–654.

Primary Examiner—John M. Ford

Attorney, Agent, or Firm—Wegner & Bretschneider

[57] ABSTRACT

The invention relates to compounds of the general formula I

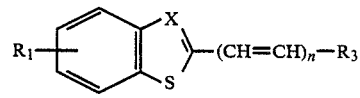

wherein
$R_1$ represents one up to and including four, the same or different substituents selected from alkyl(1–6 C), alkoxy(1–6 C), hydroxy, halogen, $NO_2$, $CF_3$ or the group $-NR_5R_6$, whereby two substituents taken together may also represent a methylene-dioxy group,
X represents nitrogen or the group

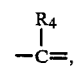

n has the value 0, 1 or 2,
$R_3$ represents one of the moieties:

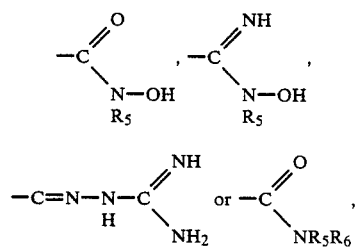

the latter meaning of $R_3$ (amide) only under the condition that for X is nitrogen the meaning of $R_1$ is limited to substituents selected from hydroxy, alkoxy(1–6 C) and methylenedioxy, and $R_4$, $R_5$ and $R_6$ represent hydrogen or alkyl(1–6 C), and pharmaceutically acceptable salts thereof, suitable in the treatment of heart failure.

17 Claims, No Drawings

POSITIVE INOTROPHIC BENZOTHIAZOLE AND BENZOTHIOPHENE COMPOSITIONS AND METHOD OF USE THEREFOR

RELATED APPLICATIONS

This application is a continuation of U.S. application Ser. No. 07/140,953, filed December 28, 1987, now abandoned, which is a continuation of U.S. application Ser. No. 07/000,466, filed January 5, 1987, now abandoned, which is a divisional of U.S. application Ser. No. 06/709,396, filed March 7, 1985, now U.S. Pat. No. 4,665,206.

The invention relates to compounds of the general formula I

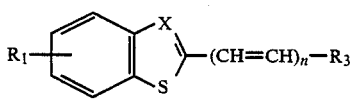

wherein
$R_1$ represents one up to and including four, the same or different substituents selected from alkyl(1–6 C), alkoxy(1–6 C), hydroxy, halogen, $NO_2$, $CF_3$ or the group $-NR_5R_6$,
whereby two substituents taken together may also represent a methylene-dioxy group,
X represents nitrogen or the group

n has the value 0, 1 or 2,
$R_3$ represents one of the moieties:

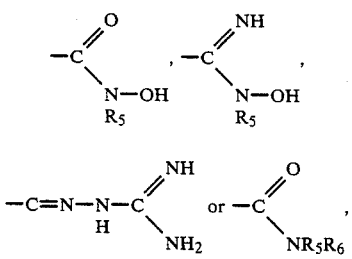

the latter meaning of $R_3$ (amide) only under the condition that for X is nitrogen the meaning of $R_1$ is limited to substituents selected from hydroxy, alkoxy(1–6 C) and methylenedioxy, and $R_4$, $R_5$ and $R_6$ represent hydrogen or alkyl(1–6 C) and pharmaceutically acceptable salts thereof.

The compounds according to the invention have a cardiotonic activity and more particularly they show a very potent increase of the force and energy of the heart-muscular contractions (positive inotropic effect).

The compounds of the invention may be prepared by any method known for the preparation of analogous compounds.

A very suitable starting product for the preparation of the compounds I is a compound of the formula II

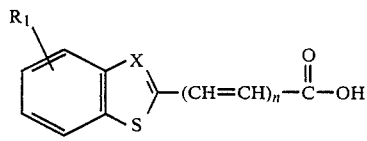

wherein $R_1$, n and X have the aforesaid meanings.

Compounds of the invention in which $R_3$ represents the moiety

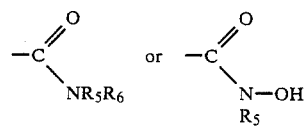

may for example be prepared by reacting the compound of formula II or an acid halide or anhydride thereof with an amine of the formula III or hydroxylamine of the formula V:

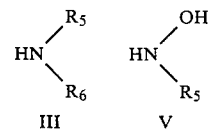

in which $R_5$ and $R_6$ have the aforesaid meaning, or a reactive derivative thereof, in which the hydrogen atom is replaced by a more reactive moiety, such as an alkali metal.

Compounds of formula I, in which $R_3$ represents the moiety

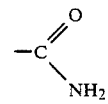

may also be prepared by reacting a compound of formula II or an acid halide or anhydride thereof with an alkali metal azide, followed by reduction of the resulting azide.

Compounds of the invention in which $R_3$ represents a

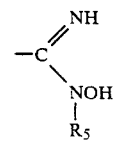

moiety may, for example, be prepared from a nitrile of the general formula IV:

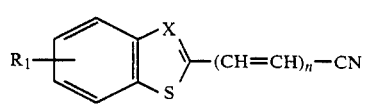

in which $R_1$, X and n have the meanings assigned before by reacting the said nitrile in the usual manner with a compound of the formula V:

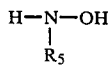

wherein $R_5$ has the aforesaid meanings, or a reactive derivative thereof, in which hydrogen (at the nitrogen atom) has been replaced by a more reactive moiety, such as an alkali metal.

The nitrile of formula IV may be prepared in the usual manner from the corresponding carboxylic acid of formula II by converting the carboxylic acid into the corresponding carboxamide followed by dehydratation of the carboxamide.

Compounds of the invention, in which $R_3$ represents a —C≡N—NH—C(=NH)NH$_2$ moiety, may most conveniently be prepared from an aldehyde of the formula:

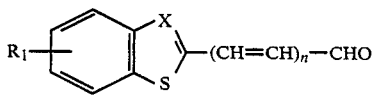

by condensation of this compound (VI) with amino guanidine or a salt thereof.

The aldehyde of formula VI can be prepared in various manners. For example the aldehyde may be manufactured by reducing the carboxylic acid of formula II in a well known manner.

Another convenient synthesis for preparing the aldehyde consists of a mild reduction of the corresponding nitrile of formula II, e.g. with the aid of a metal hydride such as diisobutylaluminiumhydride.

The starting product of general formula II may be prepared by known methods. The attached flow sheet shows the preparation of a compound of formula II, wherein n=0. Chain length extension to n=1 and n=2 can be obtained by converting the carboxylic acid II (n=0) into the corresponding aldehyde (n=0) and reacting said aldehyde with the appropriate phosphonate-ylid using reaction conditions well known in carrying out the Witting reaction.

Appropriate phosphonate ylids are, for example, cyanomethylene triphenylphosphorane, carboxymethylene triphenylphosphorane and corresponding (alkyl)esters, and 3-cyano propen(2)-ylidene triphenylphosphorane. If necessary, the nitrile—obtained through this Witting reaction—can be converted into the corresponding amide or carboxylic acid.

Preferably most substituents at the benzoring (see $R_1$) are already present in one of the starting products. Nevertheless it is very well possible to convert a substituent $R_1$ into another substituent $R_1$ after the above mentioned condensation reactions.

Thus, one or more hydroxy groups ($R_1$) may be converted into the corresponding alkoxy groups or halogen in the usual manner. Furthermore two hydroxy groups may be converted into one methylene-dioxy group and an alkoxy group may be hydrolysed to the corresponding hydroxy group.

The compounds according to the general formula I may be converted into a pharmaceutically acceptable salt.

The compounds of formula I which have an alkaline character may be obtained as the free base or as an acid addition salt. If required, however, the free base I can be prepared from the salt, for example by reaction with an alkaline compound or by means of an ion exchanger, whilst the free base I can be converted in a simple manner into an acid addition salt.

Pharmaceutically acceptable acid addition salts are derived from acids, such as hydrochloric acid, sulphuric acid, phosphoric acid, acetic acid, propionic acid, glycolic acid, maleic acid, fumaric acid, malonic acid, succinic acid, tartaric acid, lactic acid, citric acid, ascorbic acid, salicylic acid, benzoic acid and methane-sulphonic acid.

Compounds I having an acidic nature may be converted into a metal salt, preferably an alkali metal salt such as the sodium salt.

By the term "alkyl(1–6 C)" as used in the definitions of $R_1$, $R_4$, $R_5$ and $R_6$ is meant a saturated hydrocarbon with 1 to 6 carbon atoms, and preferably 1 to 4 carbon atoms, such as methyl, ethyl, propyl, isopropyl, butyl, isobutyl, tert. butyl, pentyl and isopentyl.

An alkoxy(1–6 C) group is an alkyloxy group, in which the term alkyl has a similar meaning as above.

By halogen in the definition of $R_1$ is preferably meant iodine, bromine, chlorine and fluorine. The most preferred halogens are chlorine and bromine.

The said compounds in accordance with the invention can be administered either orally, locally or parenterally, preferably in a daily dose between 0.01 and 50 mg/kg body weight. For this purpose the compounds are processed in a form suitable for oral, local or parenteral administration, for example a tablet, pill, capsule, solution, suspension, emulsion, paste or spray. The oral form is the most preferred form of administration.

The most potent inotropic compounds are found amongst those compounds of formula I in which at least two substituents $R_1$ are present selected from hydroxy or alkoxy or in which at least one methylene-dioxy group ($R_1$) is present, whereby the dimethoxy or methoxy-hydroxy substitution pattern is most preferred.

Preferred compounds of formula I are moreover those compounds I in which X is —CH=.

The position of the double bond between nitrogen and carbon in some of the moieties defined by $R_3$ of formula I cannot be clearly specified, because an equilibrium will prevail between:

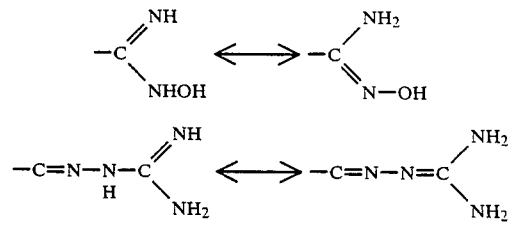

The preferred $R_3$ moiety in the compounds of the invention is the amide moiety and especially the N-hydroxy-(carbox)imidamide moiety.

The preferred value of n is 0 or 1.

EXAMPLE 1

5,6-Dimethoxy-benzo[b]thiophene-2-carboxamide.

A mixture of 5,6-dimethoxy-benzo[b]thiophene-2-carboxylic acid (68.8 g), dry toluene (350 ml), thionyl chloride (126 ml) and pyridine (1.75 ml) was stirred and heated at reflux for 4 hours. The resultant mixture was cooled, evaporated to dryness under vacuum and the residue was purged with dry toluene (3×250 ml). The resulting crude acid chloride was suspended in dioxan (160 ml) then cooled in an ice bath and treated in one portion with concentrated ammonium hydroxide solution (33% w/w, 900 ml). This gave a suspension of brown solid which was stirred for two hours then filtered, washed with water and dried under vacuum over calcium chloride at 60° C. to give 5,6-dimethoxy-benzo[b]thiophene-2-carboxamide (62.5 g), m.p. 211°–213° C.

EXAMPLE 2

A. 5,6-Dimethoxy-benzo[b]thiophene-2-carbonitrile.

5,6-Dimethoxy-benzo[b]thiophene-2-carboxamide (65 g) was suspended in pyridine (325 ml). The solution was cooled to 0° C. and treated dropwise with trifluoro acetic anhydride (185 ml) whilst maintaining the internal reaction temperature below 10° C. The mixture was then stirred at room temperature for 30 min. then cooled and treated dropwise with water (170 ml) whilst maintaining the internal temperature below 30° C. The reaction mixture was diluted with more water (800 ml), stirred and the brown solid was filtered and dried under vacuum over calcium chloride at 60° C. Recrystallisation from acetone/ether afforded 5,6-dimethoxy-benzo[b]thiophene-2-carbonitrile as a white solid (47 g), m.p. 125° C.

B. N-Hydroxy-5,6-dimethoxy-benzo[b]thiophene-2-carboximidamide

Sodium metal (1.86 g) was cut into small pieces and added to a stirred methanol solution (30 ml) under an atmosphere of nitrogen. When all the sodium had dissolved the hot solution was treated with a warm solution of hydroxylamine hydrochloride (5.65 g) in methanol (40 ml). After 1 h. the white suspension of sodium chloride was filtered off and the filtrate was added to 5,6-dimethoxy-benzo[b]thiophene-2-carbonitrile (6.0 g). The solution was stirred at 50° C. for 3 hours then cooled, diluted with water (400 ml), stirred and the white solid filtered and dried to give N-hydroxy-5,6-dimethoxy-benzo[b]thiophene-2-carboximidamide (6.74 g), m.p. 216°–219° C. (decomp.).

The free base was dissolved in methanol (120 ml), stirred, and the solution was saturated with hydrogen chloride gas. After 5 min. the solution was concentrated, diluted with ether and the white solid was filtered. Recrystallisation from methanol:ether (1:2) afforded pure N-hydroxy-5,6-dimethoxy-benzo[b]thiophene-2-carboximidiamide hydrochloride (6.8 g), m.p. 203°–210° C. Melting point mesylate salt: 211°–212° C.

EXAMPLE 3

A. 5,6-Dihydroxy-benzo[b]thiophene-2-carbonitrile.

5,6-Dimethoxy-benzo[b]thiophene-2-carbonitrile (9.0 g) was dissolved in dichloromethane (135 ml) and the solution was stirred and cooled to −70° C. and treated at a rapid dropwise rate with a cold solution of boron tribromide (19.5 ml) in dichloromethane (60 ml). The resultant suspension was stirred at room temperature for 1 h. then poured into ice-cold water (1000 ml). The light coloured solid was filtered, dried, dissolved in acetone:hexane (1:1) then eluted through coarse silica (0.2–0.5 mm, Merck, 50 g) in acetone:hexane (1:1). The appropriate fractions were combined, evaporated to dryness and crystallised from acetone/n-hexane to give 5,6-dihydroxy-benzo[b]thiophene-2-carbonitrile (7.5 g), m.p. 229°–230° C.

B. N-5,6-Trihydroxy-benzo[b]thiophene-2-carboximidamide hydrochloride.

Using the procedure described in Example 2B, 5,6-dihydroxy-benzo[b]thiophene-2-carbonitrile was converted into N-5,6-trihydroxy-benzo[b]thiophene-2-carboximidamide hydrochloride.

Free base, m.p. 188°–190° C. (decomp.).
Hydrochloride, m.p. 200°–205° C. (decomp.).

EXAMPLE 4

A. Thieno[2,3-f]-1,3-benzodioxole-6-carbonitrile.

A mixture of powdered potassium hydroxide (12.36 g) and dimethylsulphoxide (100 ml) was stirred at room temperature for 5 min. then treated with 5,6-dihydroxy-benzo[b]thiophene-2-carbonitrile (5.26 g). After 1 minute di-iodomethane (4.4 ml) was added and the suspension was stirred at room temperature for 75 minutes, then more di-iodomethane (2.2 ml) was added. After a further 30 minutes the reaction was poured into water (500 ml) and extracted with ethyl acetate (2×100 ml). The organic extracts were combined, washed with 2M HCl and saturated brine, then dried and evaporated to give a brown crystalline residue. The crude product was suspended in hot dichloromethane (200 ml), filtered, and the filtrate was passed through a column of silica gel (0.2–0.5 mm, Merck, 25 g). The appropriate fractions were combined and evaporated to dryness to give a white solid (3.4 g). Crystallisation from acetone/ether afforded pure thieno[2,3-f]-1,3-benzodioxole-6-carbonitrile, m.p. 179°–180° C.

B. N-Hydroxy-thieno[2,3-f]-1,3-benzodioxole-6-carboximidamide hydrochloride.

Using the method described in Example 2B thieno[2,3-f]-1,3-benzodioxole-6-carbonitrile was converted into N-hydroxy-thieno[2,3-f]-1,3-benzodioxole-6-carboximidamide hydrochloride.

Free base; m.p. 229°–231° C. (decomp.).
Hydrochloride, m.p. 200°–203° C. (decomp.).

EXAMPLE 5

N-Hydroxy-5,6-dimethoxy-N-methyl-benzo[b]thiophene-2-carboximidamide hydrochloride.

Sodium metal (0.40 g) was cut into small pieces and added to a stirred solution of methanol (30 ml) under an atmosphere of nitrogen. When all the sodium had dissolved the solution was treated with a solution of N-methylhydroxylamine HCl (1.45 g) in methanol (30 ml). After 30 minutes the white suspension of sodium chloride was filtered off and the filtrate was added to 5,6-dimethoxy-benzo[b]thiophene-2-carbonitrile (4.0 g). The resultant solution was stirred and heated at reflux for 5 hours then evaporated to dryness. The residue was chromatographed through a column of course silica (0.2–0.5 mm, Merck, 150 g) in dichloromethane:methanol (85:15 v/v). The appropriate fractions were combined and evaporated to dryness to give N-hydroxy-5,6-dimethoxy-benzo[b]thiophene-2-carboximidamide as a white solid (3.6 g). The free base was dissolved in ethyl alcohol (25 ml) and dichloromethane (25 ml) then treated with a solution of dry ether (200 ml) saturated with HCl gas. The precipitated yellow solid was filtered and recrystallised from ethyl alcohol to give N-hydroxy-5,6-dimethoxy-N-methyl-benzo[b]thiophene-2-carboximidamide hydrochloride (2.9 g), m.p. 237°–241° C. (decomp.).

EXAMPLE 6

A. 5,6-Dimethoxy-benzo[b]thiophene-2-carboxaldehyde.

5,6-Dimethoxy-benzo[b]thiophene-2-carbonitrile (2.0 g) was suspended in dry toluene (40 ml) under an atmosphere of nitrogen. The reaction mixture was cooled to −5° C. and treated dropwise with a solution of diisobutylaluminium hydride in toluene (1.5M, 13 ml). After 30 minutes the solution was treated with methanol (5 ml) then poured into hydrochloric acid (1M, 200 ml) and stirred for 15 minutes. The resultant solution was extracted into dichloromethane (4×100 ml) then the organic extracts were combined, washed with brine, dried over magnesium sulphate and evaporated to dryness. The orange residue (1.6 g) was crystallised from dichloromethane:ether to give 5,6-dimethoxy-benzo[b]thiophene-2-carboxaldehyde as a white solid, m.p. 155°–156° C.

B. 3-(5,6-Dimethoxy-benzo[b]thiophene-2-yl)-2-propenenitrile.

Cyanomethylene-triphenylphosphorane was prepared according to the method of S. Trippett and D. M. Walker [J.C.S., 1959, 3874–3876] and S. S. Novikov and G. A. Shvekhgeimer [C.A., 1961, 55, 13353 g].

A mixture of 5,6-dimethoxybenzo[b]thiophene-2-carboxaldehyde (8.14 g) and cyanomethylene triphenylphosphorane (22.06 g) in dry toluene (270 ml) was stirred and heated to reflux for 1 hour. The reaction mixture was then evaporated to dryness and the residue was dissolved in a mixture of dichloromethane (50 ml) and toluene (50 ml) and passed through a column of coarse silica (0.2–0.5 mm, Merck, 600 g). The column was eluted with toluene:ethyl acetate (4:1 v/v). The appropriate fractions were combined and evaporated to dryness and the residue was crystallised from dichloromethane:diethyl ether to give pure (E)-3-(5,6-dimethoxy-benzo[b]thiophene-2-yl)-2-propenenitrile (7.56 g), m.p. 154°–158° C.

C. N-Hydroxy-3-(5,6-dimethoxy-benzo[b]thiophene-2-yl)-prop-2-ene-imidamide hydrochloride.

Using the procedure described in Example 2 (E)-3-(5,6-dimethoxy-benzo[b]thiophene-2-yl)-2-propenenitrile was converted into (E)-N-hydroxy-3-(5,6-dimethoxy-benzo[b]thiophene-2-yl)-prop-2-eneimidamide hydrochloride, m.p. 188°–198° C. (decomp.).

EXAMPLE 7

A. 4-Chloro-5,6-dimethoxy-benzo[b]thiophene-2-carboxylic acid.

2-(3,4-Dimethoxyphenyl)-1-mercapto-acrylic acid (165.0 g) (Tetrahedron, 1969, 25, 2781–2785) was dissolved in dry dioxan (800 ml) and the solution was stirred and heated at 60° C. A solution of chlorine (87 g) in carbon tetrachloride (700 ml) was then added over 30 min. After a further 45 min. the reaction mixture was concentrated under reduced pressure and the residue was triturated with acetone. The resultant pale yellow solid was filtered and dried at 65° C. to give about a 1:1 mixture of 5,6-dimethoxy-benzo[b]thiophene-2-carboxylic acid and 4-chloro-5,6-dimethoxy-benzo[b]thiophene-2-carboxylic acid. The crude product (113 g) was suspended in ethanol (850 ml) and the mixture was stirred and treated over 5 min. with hydrogen chloride gas. The resultant suspension was refluxed for 5 hours and then evaporated to dryness. The crystalline residue was purified by chromatography through silica (0.2–0.5 mm, Merck, 1.5 kg) in toluene:ethyl acetate 19:1. The appropriate fractions were combined and evaporated to dryness to give 4-chloro-5,6-dimethoxy-benzo[b]thiophene-2-carboxylic acid ethyl ester as a white solid (35 g). A portion crystallised from dichloromethane/methanol had m.p. 124°–126° C.

4-Chloro-5,6-dimethoxy-benzo[b]thiophene-2-carboxylic acid ethyl ester (29.5 g) was suspended in a mixture of methanol (450 ml), water (75 ml) and potassium carbonate (20.4 g) under an atmosphere of nitrogen. The reaction mixture was heated at reflux for 1 hour then cooled and poured into water (2.5 liter) containing hydrochloric acid (5M, 60 ml). The resultant white solid was filtered and dried at 65° C. under vacuum to give 4-chloro-5,6-dimethoxy-benzo[b]thiophene-2-carboxylic acid (26.8 g). A portion crystallised from dichloromethane:methanol had, m.p. 267°–270° C.

B. 4-Chloro-5,6-dimethoxy-benzo[b]thiophene-2-carboxamide.

Using the procedure described in Example 1, 4-chloro-5,6-dimethoxy-benzo[b]thiophene-2-carboxylic acid was converted into 4-chloro-5,6-dimethoxy-benzo[b]thiophene-2-carboxamide, m.p. 180°–182° C.

EXAMPLE 8

A. 4-Chloro-5,6-dimethoxy-benzo[b]thiophene-2-carbonitrile.

Using the procedure described in Example 2A, 4-chloro-5,6-dimethoxy-benzo[b]thiophene-2-carboxamide was converted into 4-chloro-5,6-dimethoxy-benzo[b]thiophene-2-carbonitrile, m.p. 159°–160° C.

B. 4-Chloro-N-hydroxy-5,6-dimethoxy-benzo[b]thiophene-2-carboximidamide hydrochloride.

Using the procedure described in Example 2B, 4-chloro-5,6-dimethoxy-benzo[b]thiophene-2-carbonitrile was converted into 4-chloro-N-hydroxy-5,6-dimethoxy-benzo[b]thiophene-2-carboximidamide hydrochloride, m.p. 191°–195° C.

EXAMPLE 9

A. 5,6-Dimethoxy-benzo[b]thiophene-2-carboxylic acid ethyl ester.

5,6-Dimethoxy-benzo[b]thiophene-2-carboxylic acid (10 g) was suspended in ethanol (80 ml) and the mixture was stirred and heated at reflux for 5 hours. The resultant solution was evaporated to dryness and then crystallised from dichloromethane:methanol to give 5,6-dimethoxy-benzo[b]thiophene-2-carboxylic acid ethyl ester as a white solid (9.5 g), m.p. 84°–85° C.

B. N-Hydroxy-5,6-dimethoxy-benzo[b]thiophene-2-carboxamide.

Hydroxylamine hydrochloride (5.3 g) was dissolved in warm ethanol (100 ml). The solution was stirred under an atmosphere of nitrogen and treated with a warm solution of potassium hydroxide (6.4 g) in ethanol (50 ml). After 10 min. a solution of 5,6-dimethoxy-benzo[b]thiophene-2-carboxylic acid ethyl ester (10 g) in ethanol (250 ml) was added and the resultant mixture was allowed to stand at room temperature for 72 hours. The resultant suspension was filtered to remove the precipitated potassium chloride and the filtrate was evaporated to dryness. The resultant yellow residue was dissolved in water (250 ml), filtered and the filtrate was acidified with 5M hydrochloric acid. The precipitated product was filtered and dried at 65° C. under vacuum to give N-hydroxy-5,6-dimethoxy-benzo[b]thiophene-2-carboxamide (8.3 g). A portion crystallised from acetone had a melting point: 179°–180° C.

C. N-Hydroxy-5,6-dimethoxy-benzo[b]thiophene-2-carboxamide sodium salt monohydrate.

N-Hydroxy-5,6-dimethoxy-benzo[b]thiophene-2-carboxamide (2.5 g) was added to a stirred solution of sodium metal (0.227 g) in methanol (55 ml). After 15 min. the solution was evaporated to dryness and the residue crystallised from methanol:ether to give N-hydroxy-5,6-dimethoxy-benzo[b]thiophene-2-carboxamide sodium salt monohydrate (2.7 g), m.p. 170°–185° C. (decomp.).

EXAMPLE 10

5,6-Dimethoxy-benzo[b]thiophene-2-carboxaldehyde-amino-iminomethyl hydrazone hydrochloride.

Aminoguanadinium hydrogen carbonate (2.5 g) was suspended in methanol (35 ml) and the mixture was treated with 5M hydrochloric acid until all the solid had dissolved. The resultant solution was added to a suspension of 5,6-dimethoxy-benzo[b]thiophene-2-carboxaldehyde (4.0 g) in ethanol (40 ml) and the mixture was stirred at room temperature for 16 hours under an atmosphere of nitrogen. The white suspension was then diluted with diethyl ether (250 ml) and the white solid was filtered and dried to give 5,6-dimethoxy-benzo[b]-thiophene-2-carboxaldehyde-amino-iminomethyl hydrazone hydrochloride (5.3 g). A portion crystallised from methanol:acetone had m.p. 271°–274° C.

EXAMPLE 11

A. 4-Chloro-5,6-dimethoxy-benzo[b]thiophene-2-carboxaldehyde.

Using the procedure described in Example 6A, 4-chloro-5,6-dimethoxy-benzo[b]thiophene-2-carbonitrile was converted into 4-chloro-5,6-dimethoxy-benzo[b]-thiophene-2-carboxaldehyde, m.p. 164°–165° C.

B. 4-Chloro-5,6-dimethoxy-benzo[b]thiophene-2-carboxaldehyde-amino-iminomethyl hydrazone hydrochloride.

Using the procedure described in Example 10, 4-chloro-5,6-dimethoxy-benzo[b]thiophene-2-carboxaldehyde was converted into 4-chloro-5,6-dimethoxy-benzo[b]thiophene-2-carboxaldehyde-amino-iminomethyl hydrazone hydrochloride, m.p. 255°–265° C. (decomp.).

EXAMPLE 12

In a similar manner as described in Example 6 was prepared:
N-hydroxy-3-(4-chloro-5,6-dimethoxy-benzo[b]thiophene-2-yl)prop-2-ene imidamide; HCl salt m.p. 192°–198° C. (dec), and mesylate salt m.p. 148°–151° C.

In a similar manner as described in Example 2 were prepared the following compounds all being substituted derivatives of the basic molecule:
N-hydroxy-benzo[b]thiophene-2-carboximidamide:

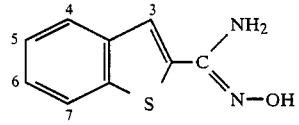

viz..
3-methyl-5,6-dimethoxy; HCl salt: m.p. 226°–232° C. (dec.);
5,6-dichloro; HCl salt: m.p. 199°–215° C. (dec.);
6,7-dichloro; HCl salt: m.p. 187°–190° C.;
4,7-dichloro-5,6-dimethoxy; HCl salt: m.p. 172°–196° C. (dec.);
7-chloro-5,6-dimethoxy; HCl salt: m.p. 166°–184° C. (dec.);
5-hydroxy-6-methoxy; HCl salt: m.p. 206°–207° C. (dec.);
6-hydroxy-5-methoxy; HCl salt: m.p. 219°–220° C. (dec.);
4-chloro-5-hydroxy-6-methoxy; HCl salt: m.p. 190° C. (dec.);;
4,7-dimethoxy; HCl salt: m.p. 158°–178° C. (dec.);
4,5-dimethoxy; HCl·salt: m.p. 173°–198° C. (dec.);
4-chloro-5-ethoxy-6-methoxy; HCl salt: m.p. 149°–166° C. (dec.);
5,7-dimethoxy; HCl salt: m.p. 190°–194° C. (dec.);
6-chloro-5,7-dimethoxy; HCl salt m.p. 212°–215° C. dec;
5-butoxy-4-chloro-6-methoxy; HCl salt 157°–166° C. dec;
5-ethoxy-6-methoxy; HCl salt: m.p. 208°–212° C. dec;
4-chloro-5,6-dihydroxy; HCl salt: m.p. 230° C. dec;
5,6-dimethoxy-4-nitro; mesylate salt 236°–237° C. dec;
5,6-dimethoxy-7-nitro; mesylate salt 214°–216° C. dec;
4-chloro-5,6-dimethoxy; mesylate salt 204°–210° C. dec;
4-amino-5,6-dimethoxy; HCl salt m.p. 193–195 (dec.).

EXAMPLE 13

5,6-Dimethoxy-benzothiazole-2-carboxamide

1. A solution of potassium hydroxide (30 g) in ethanol (200 ml) was saturated with dry hydrogen sulphide. The solution was diluted with a solution of potassium hydroxide (30 g) in ethanol (200 ml) and stirred under nitrogen whilst cooled with an ice/water bath. To this was added dropwise, a solution of trichloroacetamide (37 g) in ethanol (200 ml) and the red mixture was stirred under nitrogen at room temperature for 10 minutes. To this was added a solution of chloroacetic acid (32 g) in water (200 ml) which had been first neutralised with potassium carbonate. The resulting red mixture was stirred vigorously for 10 min., allowed to stand for 30 min. and the inorganic salt was removed by filtration. The filtrate (a solution of carbamoyl-thiocarbonyl-thioacetic acid) was used without delay for further conversion.

2. The solution of carbamoyl-thiocarbonyl thioacetic acid prepared above was added to a solution of 3,4-dimethoxy-aniline (20 g) in ethanol (100 ml) and water (100 ml). The mixture was allowed to stand in a sealed vessel for 2 hr. The ethanol was evaporated under reduced pressure until crystallisation occurred. The product was collected by filtration, washed with cold ethanol, and dried to give N-(carbamoyl-thiocarbonyl-)-3,4-dimethoxy-aniline (14.13 g); m.p. 149°–151° C.

3. A solution of N-(carbamoyl-thiocarbonyl-)-3,4-dimethoxy-aniline (14 g) in 12% aqueous potassium hydroxide solution (1.26 l) was added slowly to a stirred solution of potassium ferricyanide (251.5 g) in water (560 ml) cooled to 10° C. The thick, yellow precipitate formed was stirred for 30 min., collected by filtration, washed with water, and dried. Crystallisation from dichloromethane/ethanol gave 5,6-dimethoxy-benzothiazole-2-carboxamide (11.98 g); m.p. 211°–212° C.

EXAMPLE 14

N-Hydroxy-5,6-dimethoxy-benzothiazole-2-carboximidamide hydrochloride.

Using the procedure described in Example 2A, 5,6-dimethoxy-benzothazole-2-carboxamide was converted to 5,6-dimethoxy-benzothiazole-2-carbonitrile, m.p. 176°–177° C.

In an analogous manner as described in Example 2B, 5,6-dimethoxy-benzothiazole-2-carbonitrile was converted to N-hydroxy-5,6-dimethoxy-benzothiazole-2-carboximidamide hydrochloride; m.p. 230°–232° C. and then converted into its hydrochloride, m.p. 205°–208° C.

We claim:

1. A pharmaceutical composition providing a positive inotropic effect to a subject which comprises an inotropically effective amount of a compound of the formula

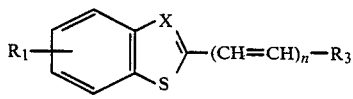

wherein
each $R_1$ is independently alkyl (1–6 C), alkoxy (1–6 C), hydroxy, halogen, $NO_2$, $CF_3$ or the group $-NR_5R_6$, or two adjacent substituents taken together may form a single methylene dioxy group,
m is from 1 to 4,
X represents nitrogen or the group

n has the value 0, 1 or 2, $R_3$ represents one of the moieties:

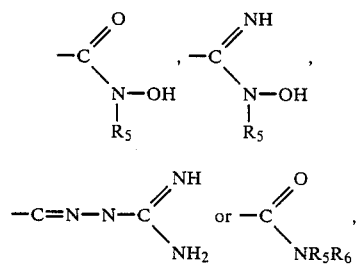

the latter meaning of $R_3$ (amide) only under the condition that for X is nitrogen the meaning of $R_1$ is limited to substituents selected from hydroxy, alkoxy (1–6 C) and methylene dioxy, and $R_4$, $R_5$ and $R_6$ represent hydrogen or alkyl (1–6 C) and pharmaceutically acceptable salts thereof in admixture with a pharamaceutically acceptable carrier therefor.

2. A composition of claim 1 comprising an positive inotropically effective amount of a compound wherein m is greater than one and at least two of $R_1$ are alkoxy or hydroxy.

3. A composition of claim 2 comprising an positive inotropically effective amount of a compound wherein m is two and the two $R_1$ groups are methylene dioxy.

4. A composition of claim 2 comprising an positive inotropically effective amount of a compound wherein each $R_1$ is methoxy.

5. A composition of claim 2 comprising an positive inotropically effective amount of a compound wherein one $R_1$ is methoxy and the other $R_1$ is hydroxy.

6. A composition of claim 1 comprising an positive inotropically effective amount of N-hydroxy-5,6-dimethoxy-benzo[b]thiophene-2-carboximidamide or pharmaceutically acceptable salts thereof.

7. A composition of claim 1 comprising an positive inotropically effective amount of 4-chloro-N-hydroxy-5,6-dimethoxy-benzo[b]thiophene-2-carboximidamide or pharmaceutically acceptable salts thereof.

8. A composition of claim 1 comprising an positive inotropically effective amount of 5,6-dimethoxy-benzo[b]thiophene-2-carboximidamide or pharmaceutically acceptable salts thereof.

9. A method of providing a positive inotropic effect in a patient in need of inducement of positive inotropic effect which comprises administering to said patient a positive inotropically effective amount of a composition of claim 1.

10. A method of providing a positive inotropic effect in a patient in need of inducement of positive inotropic effect which comprises administering to said patient a positive inotropically effective amount of a composition of claim 2.

11. A method of providing a positive inotropic effect in a patient in need of inducement of positive inotropic effect which comprises administering to said patient a positive inotropically effective amount of a composition of claim 3.

12. A method of providing a positive inotropic effect in a patient in need of inducement of positive inotropic effect which comprises administering to said patient a positive inotropically effective amount of a composition of claim 4.

13. A method of providing a positive inotropic effect in a patient in need of inducement of positive inotropic effect which comprises administering to said patient a positive inotropically effective amount of a composition of claim 5.

14. A method of providing a positive inotropic effect in a patient in need of inducement of positive inotropic effect which comprises administering to said patient a positive inotropically effective amount of a composition of claim 6.

15. A method of providing a positive inotropic effect in a patient in need of inducement of positive inotropic effect which comprises administering to said patient a positive inotropically effective amount of a composition of claim 7.

16. A method of providing a positive inotropic effect in a patient in need of inducement of positive inotropic effect which comprises administering to said patient a positive inotropically effective amount of a composition of claim 8.

17. A method of claim 9 wherein the composition is administered orally.

* * * * *

UNITED STATES PATENT AND TRADEMARK OFFICE
CERTIFICATE OF CORRECTION

PATENT NO. : 4,929,636

DATED : May 29, 1990

INVENTOR(S) : James REDPATH et al.

It is certified that error appears in the above-identified patent and that said Letters Patent is hereby corrected as shown below:

Claim 1. A pharmaceutical composition providing a positive inotropic effect to a subject which comprises an inotropically effective amount of a compound of the formula

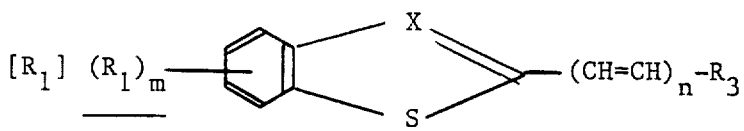

wherein each $R_1$ is independently alkyl (1-6 c), alkoxy (1-6 C), hydroxy, halogen, $NO_2$, $CF_3$ or the group $-NR_5R_6$, or two adjacent substituents taken together may form a single methylene dioxy group, m is from 1 to 4, X represents nitrogen or the group

n has the value 0, 1 or 2, $R_3$ represents one of the moieties:

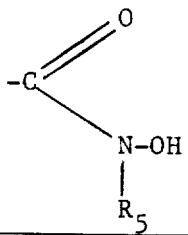          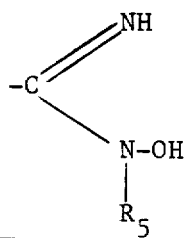

UNITED STATES PATENT AND TRADEMARK OFFICE
CERTIFICATE OF CORRECTION

PATENT NO. : 4,929,636

DATED : May 29, 1990

INVENTOR(S) : James REDPATH et al.

It is certified that error appears in the above-identified patent and that said Letters Patent is hereby corrected as shown below:

Claim 1 continued

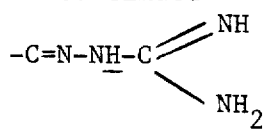  or  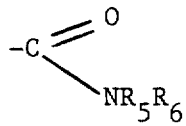

the latter meaning of $R_3$ (amide) only under the condition that for X is nitrogen the meaning of $R_1$ is limited to subtituents selected from hydroxy, alkoxy (1-6 C) and methylene dioxy, and $R_4$, $R_5$ and $R_6$ represent hydrogen of alkyl (1-6 C) and pharmaceutically acceptable salts thereof in admixture with a pharmaceutically acceptable carrier therefor.

Signed and Sealed this

Fifteenth Day of October, 1991

*Attest:*

HARRY F. MANBECK, JR.

*Attesting Officer*     *Commissioner of Patents and Trademarks*